United States Patent [19]

Hui et al.

[11] Patent Number: 4,924,019

[45] Date of Patent: May 8, 1990

[54] SYNTHESIS OF HIGH PURITY DIMETHYLALUMINUM HYDRIDE

[75] Inventors: Benjamin C. Hui, Peabody; Luis I. Victoriano, Danvers, both of Mass.

[73] Assignee: CVD Incorporated, Woburn, Mass.

[21] Appl. No.: 298,845

[22] Filed: Jan. 18, 1989

Related U.S. Application Data

[63] Continuation of Ser. No. 136,032, Dec. 21, 1987, abandoned.

[51] Int. Cl.$^5$ .................................................. C07F 5/06
[52] U.S. Cl. ..................................................... 556/187
[58] Field of Search .......................................... 556/187

[56] References Cited

U.S. PATENT DOCUMENTS

| | | | |
|---|---|---|---|
| Re. 25,179 | 5/1962 | Ziegler et al. | 556/187 X |
| 2,765,329 | 10/1956 | Lindsey | 556/187 X |
| 2,915,541 | 12/1959 | Ziegler et al. | 556/187 X |
| 2,915,542 | 12/1959 | Robinson et al. | 556/187 |
| 3,318,931 | 5/1967 | Dötzer et al. | 556/187 X |

OTHER PUBLICATIONS

Lehmkuhl et al., "Metallorganische Verbindungen", (1970), p. 58, Georg Thieme Verlag, Stuttgart.

Gaines et al., "Inorganic Synthesis", 15, p. 208, pp. 203-206.

R. Bhat et al., *J. of Crystal Growth*, 77 (1986), pp. 7-10.

Thomas Wartik et al., *Reactions of Lithium Aluminum Hydride with Representative Elements of the Main Groups of the Periodic System*, Feb. 20, 1953, pp. 835-839, J.A.C.S. 75.

*Primary Examiner*—Paul F. Shaver
*Attorney, Agent, or Firm*—Wayne E. Nacker; Gerald K. White

[57] ABSTRACT

The waste product from the synthesis of trimethylgallium is reacted with a hydride selected from an alkali metal hydride, a group IIIA hydride, or a group III hydride to produce dimethylaluminum hydride of high purity.

9 Claims, No Drawings

SYNTHESIS OF HIGH PURITY DIMETHYLALUMINUM HYDRIDE

This is a continuation of co-pending application Ser. No. 07/136,032 filed on 2/Dec. 1987 now abandoned.

The present invention is directed to a method of producing high-purity dimethylaluminum hydride, and is particularly directed to a method of producing high-purity dimethylaluminum hydride from a waste source, i.e., the residual materials from a common method of producing trimethylgallium.

BACKGROUND OF THE INVENTION

III–V films, such as Al-Ga-As films, useful for semiconducting applications, may be grown by chemical vapor deposition (CVD) as described by R. Bhat et al. J. of Crystal Growth, 77 (1986) 7-10. CVD requires a decomposable source material of each of the metallic elements to be deposited. As Bhat et al. describe, the decomposable source of aluminum has traditionally been trimethylaluminum; however, dimethylaluminum hydride is advantageous in that less carbon contamination in the film results.

Dimethylaluminum hydride (DMAH) is conventionally prepared from lithium aluminum hydride (LiAlH$_4$) (referred to herein as LAH) and trimethylaluminum (TMA) by reaction (I) as follows:

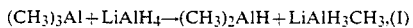

$$(CH_3)_3Al + LiAlH_4 \rightarrow (CH_3)_2AlH + LiAlH_3CH_3, (I)$$

L T. Wartick et al. J.A.C.S. 75 (1953) 835. It has also been prepared by splitting TMA under hydrogen pressure at 150-200° C.; T. Koster et al., German Democratic Republic Patent 16650 (1957); H.E. Podall et al. J. Org. Chem. 24 (1959) 1222.

Herein, is described a method of producing DMAH from the waste products of the production of a decomposable chemical, trimethylgallium (TMG), which is used as a gallium source in CVD. The conventional method of producing trimethylgallium is described by D.F. Gaines et al., *Inorganic Synthesis* 15 (1974) 203-207. Gallium trichloride is reacted with TMA according to the following reaction:

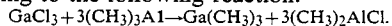

$$GaCl_3 + 3(CH_3)_3Al \rightarrow Ga(CH_3)_3 + 3(CH_3)_2AlCl.$$

Synthesis of TMG and disposal of the residual material is described as follows:

"Sodium fluoride is dried in vacuo overnight. The system (FIG. 7) [The FIGURE in this application], containing 10 g. of sodium fluoride in flask D, is flushed with dry nitrogen for at least one hour. A glass ampul containing 25 g. of gallium trichloride is placed inside a small plastic bag which has a wall thickness of at least 0.002 in. (Alternatively two bags, one inside the other, afford added protection against hydrolysis.) The bag is purged with dry nitrogen, and the ampul is subsequently crushed with a hammer. Care should be taken that the broken glass does not puncture the bag (in practice this gave little trouble). The plastic bag is placed in a large nitrogen-filled glove bag and its contents, including broken glass, are emptied into the reaction flask B. The flask is attached quickly to the rest of the reaction apparatus, and about 80 ml. of trimethylaluminum (a twofold excess) is transferred from a lecture cylinder to the addition funnel. This transfer is accomplished most readily by inverting the lecture bottle, attaching a hose connector (to which a 4-in. length of ca. 1/8-in.-o.d. stainless-steel tubing is soldered), and cautiously opening the main lecture-bottle valve after the stainless-steel tube has been inserted into the addition funnel.

The trimethylaluminum is added slowly to the gallium trichloride over a period of about one hour. The reaction is extremely exothermic and is controlled by varying the addition rate of trimethylaluminum. External cooling should be avoided, as this may adversely affect the product yield. Initially, a few drops at a time are added; later, the rate may be increased. The flask contents are stirred magnetically during the reaction and distillation.

Immediately after the addition of trimethylaluminum is completed, external heating is begun and the crude product is distilled at 55-60° onto the sodium fluoride in flask D. The pure product is redistilled at about 56° from sodium fluoride into the receiving flask F. This flask is taken from the system, quickly fitted with an adapter equipped with a stopcock, and attached to a vacuum line for transfer into a storage vessel. (Caution. Some flaming of the product may occur when the receiving flask is removed from the apparatus; however, rapid and careful work should prevent any serious problems.) Extreme caution must be exercised in the disposal of the pyrophoric residues in flask B.

The pyrophoric residues in flask B may be safely disposed of using the following procedure. After flask B has cooled to room temperature, about 900 ml. of heptane is run into it through the additional funnel A. The mixture is then stirred magnetically to ensure that all soluble residues are dissolved. The resulting 10% solution in heptane does not appear to be pyrophoric (it does smoke, however, when exposed to air). Flask B is then removed from the rest of the apparatus and its contents slowly poured onto 2-3 lb. of crushed Dry Ice contained in a 5-gal metal bucket. After the dry ice-heptane solution slurry has stood for about 0.5 hour, 1 l. of 95% ethyl alcohol is added slowly to ensure complete solvolysis. The bucket is then left undisturbed until it has warmed to room temperature.

An alternate method suggested by the checkers is as follows. After flask B has cooled to room temperature about 600 ml. of a 10% ethyl acetate solution in heptane is run slowly into it through the addition funnel A. This addition is followed by slow addition of 300 ml. of 30% ethyl acetate in heptane. The mixture is stirred magnetically until all visible reaction has ceased. The resulting solution is cautiously poured onto 5 lb. of crushed ice in a 5-gal. metal bucket to complete the hydrolysis.

Care should be taken to dilute any remaining residues with heptane as the apparatus is being disassembled for cleaning. Any solid residues remaining in the apparatus should be covered with heptane and deactivated by slow addition of pentyl alcohol until there is no further evidence of reaction."

In accordance with the invention, it is found that the waste product of the conventional synthesis of TMG, rather that being discarded, can be used as a source of producing DMAH of high purity. The resulting DMAH is easily separated from the residual materials.

SUMMARY OF THE INVENTION

In accordance with the invention, the residual or waste products from the production of trimethylgallium are reacted with a metal hydride to produce dimethylaluminum hydride. The waste product of the production of trimethylgallium primarily contains three chemical species, each of which reacts with lithium aluminum hydride to yield dimethylaluminum hydride.

The major species of the waste product is dimethylaluminum chloride which reacts with either a complex hydride of group IA and IIIA metals, an alkali metal hydride, or a group IIIA hydride to produce DMAH.

DETAILED DESCRIPTION OF CERTAIN PREFERRED EMBODIMENTS

In accordance with the invention, Applicants realized that the major waste product of the production of TMG is dimethylaluminum chloride, found that the reaction product of dimethylaluminum chloride and a metal hydride is DMAH and furthermore determined that the DMAH is readily separable from other chemical species in the reaction mixture (including other waste products of TMG production and the subsequent reduction of the dimethylaluminum chloride), whereby DMAH of high purity is achieved. The hydride may be a simple alkali metal hydride, such as sodium hydride, lithium hydride, or potassium hydride, a complex group IA-IIIA hydride, such as lithium aluminum hydride, or a group IIIA hydride such as $AlH_3$ (aluminum hydride) or $B_2H_6$ (diborane). The only limitation on group IA-IIIA hydrides is that the residual products of the reaction be readily separable from the DMAH so that high-purity DMAH may be produced.

The reaction (II) of an alkali metal hydride (MH) with dimethylaluminum chloride is:

$$MH + (CH_3)_2AlCl \rightarrow MCl + (CH_3)_2AlH.$$

Reaction (II) proceeds stoichiometrically. DMAH is a liquid having a boiling point of 154° C. DMAH is readily separable by distillation from the minor amount of TMG (B.P. 55° C.), which remains after distillation and collection of the major portion of the TMG product, and from residual trimethylaluminum (B.P. 130° C.). Unreacted metal hydride and metal chloride are solids, permitting initial separation of the liquid components therefrom, e.g., simply by decanting and/or filtering the liquid.

Because the reaction of MH with dimethylaluminum chloride is stoichiometric, it is preferred to use approximately a molar amount of MH equivalent to that of the dimethylaluminum chloride (the amount of which can be closely calculated from the reactants of the TMG-producing reaction). Slight molar excesses or deficiencies, e.g., up to about 10% of MH relative to dimethylaluminum chloride are not of significant concern because DMAH (B.P. 154° C.) is easily separated by distillation from either residual MH or dimethylaluminum chloride (B.P. 119° C). However, it is considered to be desirable to use, as closely as possible, equal molar amounts of MH and dimethylaluminum chloride to minimize the levels of pyrophoric residue, i.e., MH and dimethylaluminum chloride. An advantage of the use of a MH is the reduction in the levels of pyrophoric waste product which is left. As discussed hereinabove, substantial precautions are required for disposal of the residue of TMG production, and the conversion of dimethylaluminum chloride to product dimethylaluminum hydride greatly minimizes these disposal problems.

In accordance with a particular aspect of this invention, it was determined that the waste product of TMG synthesis leaves three metal-containing compounds, dimethylaluminum chloride as the major species, plus small amounts of trimethylaluminum and trimethylgallium, and that lithium aluminum hydride reacts with each of these compounds to produce DMAH. The reaction of TMA with LAH is set forth above (Reaction (I)). The reaction of dimethylaluminum chloride and LAH and of TMG with LAH are set forth in reactions (III) and (IV) below.

$$(CH_3)_2AlCl + LiAlH_4 \rightarrow (CH_3)_2AlH + LiAlH_3Cl \quad (III)$$
$$(CH_3)_3Ga + LiAlH_4 \rightarrow (CH_3)_2AlH + LiGaH_3CH_3 \quad (IV)$$

Thus, each of the metal-containing species reacts with LAH to yield DMAH as one of the reaction products. Again, the DMAH which is produced is easily separable from the other reaction products; $LiAlH_3Cl$, $LiGaH_3CH_3$ and $LiAlH_3CH_3$ are each solid at room temperature, and the liquid DMAH and other liquid components may be decanted and/or filtered therefrom.

To maximize production of DMAH, it is preferred to use LAH at a molar equivalent of the combined TMA, TMG, and dimethylaluminum chloride. These can be calculated. A slight deficiency, e.g., up to about 10 molar %, of LAH will merely reduce efficiency slightly (each of reactions (I), (III), and (IV) are substantially stoichiometric). A molar ratio of LAH above about molar 10% relative to the metal-containing components of the waste material is considered to be wasteful and increases disposal problems.

The use of LAH as a reactant is preferable to an alkali metal hydride (MH) from the standpoint of producing DMAH from both TMA and TMG; however, LAH is generally more expensive relative to MH's and leaves more pyrophoric waste products, for which precautions must be taken in disposal.

In the synthesis of TMG described above, very little solvent is used, and the residual material is a very viscous material. Although it is conceivable that the hydride be added to this viscous mixture to produce DMAH, it is preferred that the residual material be diluted with a suitable solvent to facilitate mixing of the solid hydride material with the liquid components. There need be no separation of the solid waste materials of TMG synthesis, prior to reaction of the hydride with the waste mixture. Suitable solvents are those which do not react with any of the reactants or other residual materials. Hydrocarbon solvents, including alphatic and aromatic solvents are useful, e.g., toluene, benzene, xylenes, hexanes, and petroleum ether are likewise suitable. Ether solvents, such as n-butyl ether are also suitable. Water and alcohols are unsuitable. In selecting a solvent, it is preferred to select one with a boiling point substantially removed from that of DMAH (154° C.) to facilitate removal by distillation.

Because of the pyrophoric nature of several of the compounds of the mixture, the reaction of the waste material from TMG material with a hydride, either simple or complex, is carried out under a dry, non-reactive atmosphere, e.g., dry nitrogen.

The reaction temperature is not considered to be critical, as the reactions will proceed readily at room temperature or above; however, as the reactions of hydrides with the waste product from the synthesis of TMG are exothermic, precautions, such as slow addition of the hydride to the waste material (or vise versa) are generally taken. If solvent is used, the reflux temperature of the solvent may be used to determine the reaction temperature.

Other complex hydrides of the IA-IIIA type may be used, including but not limited to: $NaBH_4$ (sodium borohydride), $LiBH_4$ (lithium borohydride), $LiBHR_3$, where R is a short-chain alkyl group (lithium trialkylborohydride), and NaAlH$_4$ (sodium aluminum hydride).

The only restriction on the use of other complex hydrides is that chemicals not be produced which cannot be readily separated from the DMAH. Other complex hydrides, however, do not share the advantage of lithium aluminum hydride in producing DMAH from all three metalcontaining waste compounds from TMG production, and like LAH, yield pyrophoric residues. Furthermore, the complex hydrides tend to be more expensive than alkali metal hydrides.

Also suitable for reaction with TMG reaction waste products are group III hydrides, including aluminum hydride and diborane. These react with dimethylaluminum chloride as follows:

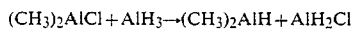

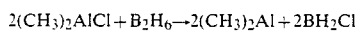

The process of the present invention is considered highly advantageous in that it utilizes material which has heretofore been considered to be waste. Utilization of this "waste" material is considered to be especially valuable in view of precautions required for disposal of the same.

A surprising and unexpected advantage of the process of the present invention is that it produces DMAH having a lower silicon content than DMAH produced according to conventional methods, i.e., from TMA. Apparently, distillation of TMG from the residual materials removes many of the silicon-containing compounds. Because silicon, like carbon, is considered detrimental to III-V films formed by CVD, the TMA produced in accordance to the inventions is considered superior to that produced from substantially pure TMA.

The invention will now be described in greater detail by way of specific example.

EXAMPLE I

From Lithium Aluminum Hydride

Liquid trimethylgallium reaction waste (480g.) containing 90% Me$_2$AlCl, 9% AlMe$_3$ and <1% TMG (all figures w/w) was placed in a 3-neck vessel which was then equipped with a constant addition funnel containing 1 l. of toluene. The solvent was added rapidly while stirring. Lithium aluminum hydride (250 g.) was added in 5–7 g. portions from a solid addition funnel at a rate such that the reaction mixture was maintained at a maximum temperature of 60° C. After completing the addition, the flask was immersed in an oil bath and further heated to 100° C for two (2) hours. After cooling, a Claisen distillation head and receiving flask was attached and the volatiles were taken off under full vacuum. The solid gray residue in the reaction flask was stored for deactivation and disposal. The flask containing the liquid phase was fitted with a fresh Claisen head and receiver; the system was evacuated and toluene was taken off at room temperature until the pressure was reduced to 2.5 mm Hg. After changing receiver, the system was fully evacuated and a 30 g. forerun was collected. The receiver was changed yet again and under similar conditions; a 206 g. main fraction was collected, heating the distillation flask to a maximum temperature of 50°.

I.R. (nujol):1820 cm$^{-1}$ broad.

NMR (benzene $\phi$) 3.20 (broad, 1H); −0.3 (s,6H).

Analysis: Si 4 ppm, and no other impurities detected by ICP.

EXAMPLE II

From Sodium Hydride

A preparation of DMAH from TMG waste and NaH is carried out as follows:

Working in a glove bag under argon atmosphere, a suspension of NaH in mineral oil is washed with pentane and dried by filtration and suction. Solid NaH powder (50 g.) is charged into a flask and added to 200 g. of trimethylgallium reaction waste diluted with 100 ml. of toluene. Again, the rate of addition is controlled by the rise in temperature of the solution. When the addition is complete, the flask is heated at 100° C. for two (2) hours. After cooling, the solid NaCl is allowed to settle and the liquid phase is decanted into a fresh flask. Isolation of the product then proceeds as per Example I. The solid NaCl contains active material, possibly NaAlMe$_3$H, and so it is suspended in toluene and deactivated by addition of isopropanol.

EXAMPLE II

From Aluminum Hydride

Under argon atmosphere, 180 grams of AlH$_3$.NMe$_3$ is dissolved in toluene (500 ml.) and the solution transferred to an addition funnel. This is then added to 200 grams of trimethylgallium reaction waste diluted with 100 ml of toluene. The rate of addition is controlled by the rise in temperature of the solution. When the addition is completed, the flask is heated at 100° C for two (2) hours. Isolation of the product is by distillation as per Example I.

While the invention has been described in terms of certain preferred embodiments, modifications obvious to one with ordinary skill in the art may be made without departing from the scope of the present invention.

Various features are set forth in the following claims:

What is claimed is:

1. A method of producing dimethylaluminum hydride that is sufficiently free of silicon-containing impurities such that the level of silicon is about 4 ppm or less and sufficiently free of other impurities such that the dimethylaluminum hydride produced is useful for depositing films by chemical vapor deposition processes, the method comprising
    reacting gallium trichloride with trimethylaluminum to produce trimethylgallium and dimethylaluminum chloride,
    separating a product trimethylgallium from a waste produce which comprises dimethylaluminum chloride, trimethylaluminum, and trimethylgallium,
    without further purifying said waste product, reacting said waste product with a material selected from the group consisting of: an alkali metal hydride, a group IIIA hydride, and a group IA-IIIA complex hydride to produce dimethylaluminum hydride, and
    separating by distillation the dimethylaluminum hydride from other components of the reaction mixture.

2. A method according to claim 1 wherein said waste product is reacted with an alkali metal hydride selected from the group consisting of lithium hydride, potassium hydride, sodium hydride, and mixtures thereof.

3. A method according to claim 1 wherein said waste product is reacted with a group IA14 IIIA complex hydride selected from the group consisting of lithium aluminum hydride, sodium borohydride, lithium borohydride, lithium trialkyl borohydride, sodium aluminum hydride, and mixtures thereof.

4. A method according to claim 1 wherein said waste product is reacted with aluminum hydride or diborane.

5. A method according to claim 1 wherein said waste product is diluted in a solvent prior to reaction with a hydride.

6. A method according to claim 1 wherein said reaction of waste product and hydride is carried out under a dry, non-reactive atmosphere.

7. A method of producing dimethylaluminum hydride that is sufficiently free of silicon-containing impurities such that the level of silicon is about 4 ppm or less and sufficiently free of other impurities such that the dimethylaluminum hydride produced is useful for depositing film by chemical vapor deposition processes, the method comprising reacting gallium trichloride with trimethylaluminum to produce trimethylgallium and dimethylaluminum chloride, separating a product trimethylgallium from a waste product which comprises dimethylaluminum chloride, trimethylaluminum, and trimethylgallium, without further purifying said waste product, reacting said waste product with lithium aluminum hydride to produce dimethylaluminum hydride, and separating by distillation the dimethylaluminum hydride from other components of the reaction mixture.

8. A method according to claim 7 wherein said waste product is diluted in a solvent prior to reaction with a hydride.

9. A method according to claim 7 wherein said reaction of waste product and hydride is carried out under a dry, non-reactive atmosphere.

* * * * *

UNITED STATES PATENT AND TRADEMARK OFFICE
CERTIFICATE OF CORRECTION

PATENT NO. : 4,924,019

DATED : May 8, 1990

INVENTOR(S) : Hui et al.

It is certified that error appears in the above-identified patent and that said Letters Patent is hereby corrected as shown below:

Column 1, line 6, "2/Dec. 1987" should be --21 Dec. 1987--.

Column 1, line 31, "L T. Wartick" should be --T. Wartick--.

Column 3, line 29, insert --(II)-- before the equation.

Column 6, line 52, "produce" should be --product--.

Column 6, line 68, "IA14 IIIA" should be --IA-IIIA--.

Column 7, line 18, "film" should be --films--.

Signed and Sealed this

Twenty-second Day of June, 1993

Attest:

MICHAEL K. KIRK

Attesting Officer

Acting Commissioner of Patents and Trademarks